United States Patent [19]
Turner

[11] Patent Number: 4,712,559
[45] Date of Patent: * Dec. 15, 1987

[54] LOCAL CURRENT CAPACITIVE FIELD APPLICATOR FOR INTERSTITIAL ARRAY

[75] Inventor: Paul F. Turner, North Salt Lake, Utah

[73] Assignee: BSD Medical Corporation, Salt Lake City, Utah

[*] Notice: The portion of the term of this patent subsequent to Jun. 2, 2004 has been disclaimed.

[21] Appl. No.: 778,325

[22] Filed: Sep. 20, 1985

Related U.S. Application Data

[63] Continuation-in-part of Ser. No. 750,408, Jun. 28, 1985.

[51] Int. Cl.$^4$ .............................................. A61N 5/02
[52] U.S. Cl. ................................... 128/422; 128/399; 128/804
[58] Field of Search ............... 128/303.13, 399, 401, 128/422, 784, 786, 804

[56] References Cited

U.S. PATENT DOCUMENTS

| | | | |
|---|---|---|---|
| 4,190,053 | 2/1980 | Sterzer | 128/399 |
| 4,204,549 | 5/1980 | Paglione | 128/804 X |
| 4,237,898 | 12/1980 | Whalley | 128/422 |
| 4,311,154 | 1/1982 | Sterzer et al. | 128/804 |
| 4,322,594 | 3/1982 | Brisson | 219/497 |
| 4,397,313 | 8/1983 | Vagvine | 128/399 |
| 4,397,314 | 8/1983 | Vagvine | 128/399 |
| 4,411,266 | 10/1983 | Cosman | 128/303.18 |
| 4,446,874 | 5/1984 | Vagvine | 128/804 |
| 4,448,198 | 5/1984 | Turner | 128/422 |
| 4,572,190 | 2/1986 | Azam et al. | 128/399 |
| 4,585,002 | 4/1986 | Kissin | 128/399 |
| 4,589,424 | 5/1986 | Vagvine | 128/804 |

OTHER PUBLICATIONS

Doss et al., "Technique for Localized Heating in Tissue"..., Med. Instr., vol. 10, No. 1, Jan.-Feb. 1976, pp. 16-21.

Primary Examiner—Edward M. Coven
Attorney, Agent, or Firm—Hubbard, Thurman, Turner and Tucker

[57] ABSTRACT

An electromagnetic hyperthermia system for heating local regions of body tissue wherein the system includes a source of electromagnetic radiation connected to a power divider for distributing radiation to several power control devices that control the electromagnetic radiation transmission. Each of the power cotrol devices is connected to several radiation applicators. The radiation applicators include the capability for capacitively coupling radiation into body tissue and further include a sensor that provides an indication of adjacent body tissue temperature. A data processor is connected to the source, the power control apparatus and the temperature sensors and control the amount of heat in accordance with a desired heating pattern.

6 Claims, 6 Drawing Figures

LOCAL CURRENT CAPACITIVE FIELD APPLICATOR FOR INTERSTITIAL ARRAY

RELATED APPLICATIONS

This application is a continuation-in-part of U.S. patent application Ser. No. 750,408 filed Jun. 28, 1985.

BACKGROUND OF THE INVENTION

1. Field of the Invention

The present invention relates generally to heating human or animal tissue (hyperthermia) and more particularly to electromagnetic radiation (EMR) apparatus for heating local areas within such living body tissue.

2. Background Information

As is generally known, death, or necrosis, of living tissue cells occurs at temperatures elevated above a normal cell temperature. Further, the death rate of such heated tissue is a function of both the temperature to which it is heated and the duration for which the tissue is held at such temperatures.

It is also well known that the elevation of temperature of living tissue can be produced with electromagnetic energy at frequencies greater than about 10 kHz.

It has been reported that some types of malignant cells may be necrosed by heating them to a temperature which is slightly below the temperature injurious to most normal cells. In addition, some types of malignant cells may be selectively heated and necrosed by hyperthermia techniques because masses of these malignant cells typically have considerably poorer blood flow and thus poorer heat dissipation properties than does the surrounding normal tissue. As a result, when normal tissue containing such malignant masses is heated by EMR (electromagnetic radiation), the resultant temperature of the malignant mass may be substantially above that of surrounding healthy cells.

Although some disagreement exists regarding exact temperatures, most malignant cells have a relatively limited temperature range in which hyperthermia is effective in causing necrosis. Below a thershold temperature of about 41.5° C. (106.7° F.) insubstantial thermal damage occurs even in those types of malignancies which have a greater sensitivity to temperature than do normal cells. In fact, at temperatures just below this threshold, growth of some types of malignancies may be stimulated. At temperatures within or above 43° to 45° C. (109.4° to 113° F.) thermal damage to most normal cells occur. A discussion of hyperthermia in the treatment of cancer is contained in "Physical Hyperthermia and Cancer Therapy" by J. Gordon Short and Paul F. Turner in the *Proceedings of the IEEE*, Vol. 68, No. 1, January, 1980 herein incorporated by reference.

Typically, EMR heating of body tissue is accomplished by holding an EMR radiator, or applicator, adjacent to, or against, exterior portions of a body, the EMR then penetrating and heating subsurface portions of tissue. However, significant amounts of energy are absorbed by surface or epidermis layers which may have to be cooled in order to prevent damage thereto by overheating.

The amount of penetration, or the depth of which EMR causes effective heating, is dependent upon the frequency of radiation.

For example, in accordance with an article by A. W. Guy, et al, published in proceedings of the IEEE, Vol. 63, No. 1, January, 1974 entitled "Therapeutic Application of Electromagnetic Power", the depth of penetration in the human muscle and fat at 100 MHz is 6.66 cm (2.62 inches) and 60.4 cm (23.8 inches), respectively, while at 915 MHz the depth of penetration is only 3.04 cm (1.2 inches) and 17.7 cm (6.97 inches), respectively.

In general, the lower the EMR frequency, the larger the applicator must be in order to effectively radiate electromagnetic energy into the tissue and, as a result, applicators for radiating electromagnetic energy below one gigahertz tend to be large in size and cumbersome to handle. Additionally, such applicators are not configured to selectively heat tumors of various sizes and shapes located well beneath the surface layers of the body being irradiated. Further, tumors, or other selected areas, shielded by a layer of boney tissue such as a skull, are difficult to effectively heat with externally applied EMR.

Invasive EMR applicators, that is, radiators which can be inserted into body tissue to levels adjacent malignant tumors, or other localized growths, for selective heating thereof, may cause nonuniform heating, or "hot spotting" at or near the surface of such applicators because of nonuniform field distributions. Such unwanted "hot spotting" is more likely to cause serious overheating when such invasive applications are operated at higher power levels in order to heat large localized growths using a single applicator. Such growths may be many times the size of the radiating area of an invasive type applicator.

An example of invasive EMR applicators are disclosed in U.S. Pat. No. 4,448,198 entitled "Invasive Hyperthermia Apparatus and Method" which discloses the application of several invasive type applicators and a method of using the apparatus to effectively heat relatively large localized areas within living body tissue, without significant hot spotting at or about the applicators.

Gammell discloses a similar apparatus in U.S. Pat. No. 4,346,715 which issued Aug. 31, 1982 includes an array of contacting metal electrodes operating the array with radio frequency energy in the range of 500 KHz in a way to cause an isothermal rotating electric field which is confined to the area of the tumor or lesion.

Doss et al. also developed an invasive electrode array described in U.S. Pat. No. 4,016,886 in April of 1977 and which produced a heating field from a fixed current field being established by connecting metal needles directly contacting the tissue. Doss teaches the operation of this apparatus at low radio frequencies below 1 MHz.

German Patent DAS No. 1143937 issued in February, 1963 describes a similar two electrode array. This apparatus also placed metal electrodes in direct contact with the body. With a grounded outer conductor, the heating field may be 3 phased causing microwave energy to have current fields parallel to, and perpendicular to the electrodes. The heating field would be locally positioned at the tips of the electrodes.

German Patent DT No. 2815156 to convert describes an electromagnetic radiating apparatus which is inserted into the tissue to apply HF (high frequency) electromagnetic waves to heat living tissues. This apparatus or probe is adapted to radiate the waves into the tissue like an antenna. Also, multiple arrays of this probe may be used. This device operates at higher frequencies (300-2000 MHz) than the other referenced devices because the inner and outer coax conductors form a monopole type radiating antenna. The earlier references operate as metal contact electrode pairs or arrays which by virtue of their contact to the tissue can induce currents to flow in the tissue. These tissue current fields terminate perpendicular to the inserted electrode surfaces.

The current fields of current are substantially parallel to the radiating shaft as is well known in the sciences for monopoles and dipoles.

Turner disclosed in U.S. Pat. No. 4,448,198 a similar apparatus and method of radiating invasive monopoles was described. This apparatus also operates at high frequencies.

The Oximetrics Corporation has developed a specially designed catheter which has an internal hollow dielectric surrounded by a metal braid which is coated with a removable outer dielectric layer. This enables the clinician to remove segments of the outer dielectric coating to provide selective contact between the metal braid and the surrounding tissues into which the catheter is inserted. This technique applies 500 KHz currents directly into the tissue to cause a local current field between electrode referenced by a presentation at North American Hyperthermia Group by S. D. Prionas, et al, "Interstitial RF Hyperthermia Plus Brachy Therapy of Neoplasma," Stanford University School of Medicine. Clinical use in stimulation of muscle and nerve tissues has shown that this apparatus requires special precautions to shape the waveform or eliminating the current field prior to switching active electrode pairs. These observations have been reported by independent researchers who have shown such stimulation is observed as high as 1 MHz. These researchers have indicated such stimulation is potentially hazardous. Some of the hazardous effects are obturator muscle spasm, cardiac ventricular fibrillation, and pacemaker malfunction referenced by John R. LaCourse, et al., "Effect of High-Frequency Current On Nerve and Muscle Tissue," IEEE transaction BME-32, No. 1, January 1985, pp. 82–86.

This results in the stimulation threshold current increasing montonically with increasing frequency. Therefore, the stimulation current at 50 MHz would be expected to be about 50 times more than the stimulation current at 1 MHz. Thus, for frequencies above 1 MHz tissue, destruction or desiccation probably occurs before the stimulus threshold current can be reached.

The use of frequency of approximately 10 MHz or more would eliminate this potentially hazardous stimulation potential.

The apparatus and methods described by Gammell, Doss, and Oximetrics use the lower frequencies near 500 KHz with contacting metallic electrodes. That of Fritz also uses contacting metal electrodes but with higher frequency microwave fields being radiated.

Convert and Turner methods patented earlier both use radiating electromagnetic waves from each electrode or applicator acting like a monopole antenna.

All these methods require metallic contact to the tissue and sterilization of the electrode or applicator. This would be difficult for repeated use since each has exposed material interfaces which would be difficult to clean after use.

The method and devices of this invention includes the use of a sterile catheter or dielectric tube placed into the tissue to enable the applicator insertion therein. The catheter would either pass completely through the tissue exposing both ends to the outside air, or the catheter would have a closed tip. The use of the high frequency selective capacitive coupling through the catheter is distinctly different from the established prior art.

The procedure to install such catheters is quite common in radiation therapy, where radioactive seeds or wire ribbons are inserted into a number of these catheters to radiate a tumor from inside with ionizing radiation. It has been shown that adding tissue heating to ionizing radiation enhances tumor cell killing and regression. The method of using the standard dielectric catheters (nylon or teflon) for local capacitive heating inside the tumor should minimize treatment costs and improve clinicians acceptance. This method is therefore a significant improvement over the direct contact applicator methods and also different from these methods.

It is the object of the present invention to provide an applicator for inserting into body tissue through a dielectric catheter or sleeve for locally heating these tissues.

It is further the object of the present invention to provide an enlarged diameter metal section for more selective heating in the intended area with reduced heating in the zones of smaller electrode diameters. This is a result of larger capacitance from the enlarged metal section through the catheter to the tissue than the capacitance of the smaller metal sections.

It is still further an object of this invention to provide a system to provide UHF electromagnetic (EM) signals capable of flowing through the catheter wall capacitive impedance.

It is still further an object of this invention to provide an applicator and system which enables the temperature of the electrodes to be measured with or without EM signals being applied to the applicator for the control of the EM power to each applicator to achieve the desired elevation of the tissue temperatures around each applicator.

SUMMARY OF THE INVENTION

In accordance with the present invention an applicator is provided for capacitive coupling electromagnetic energy into local areas of body tissue. The applicator includes an enlarged diameter metallic section for selectively coupling electromagnetic currents into the body tissue and further includes temperature sensing capability for providing an indication of the adjacent body tissue temperature.

In one embodiment of the present invention, an applicator for capacitive coupling electromagnetic energy into the local regions of body tissues is provided that includes a coaxial cable having an outer conductor shorter in length than the center conductor whereby the temperature sensing apparatus is connected between the outer and inner conductors by two long twisted wires. In this embodiment, the temperature sensing apparatus includes thermistors each having an impedance at least 100 times greater than the impedance of the applicator array at the electromagntic operating frequency and distributed along the applicator to detect temperatures in different regions. Also in this embodiment, one of these wires connects the enlarged diameter metal coupling region to the coax center conductor to increase the capacitance coupling of electromagnetic energy to the surrounding tissue.

In a further embodiment, a method for operating the hyperthermia electromagnetic capacitive coupling applicator is disclosed that includes providing an electromagnetic field of energy to the application while simultaneously providing a direct current to the applicator for determining the surrounding tissue temperature.

Still further, a method for operating the hyperthermia electromagnetic radiation applicator that includes a temperature sensing device for indicating temperature variations in the surrounding body tissue is provided that includes the steps of providing direct current energy while simultaneously and intermittently providing high frequency electromagnetic energy to the applicator. The voltage drop across the applicator is then measured both during the time that the electromagnetic energy is being applied and the time that the electromagnetic energy is absent. Since, in this method, the temperature sensing device absorbs a portion of the electromagnetic energy, the resulting measurements during the time that electromagnetic energy is absent is used to determine the temperature of the surrounding tissue. The measured voltage during the time of application of electromagnetic energy is used to determine the high frequency power output of the applicator.

In a still further embodiment of the present invention, an electromagnetic hyperthermia apparatus is provided for heating local regions of body tissue and includes a source of electromagnetic energy connected to a plurality of electromagnetic energy capacitive applicators that are inserted in the body tissue. A control apparatus is interconnected between the electromagnetic power source and each applicator that controls the amplitude and/or phase from each applicator in accordance with the temperature indicated by the applicator and a desired heating pattern. In operation, this control device varies the energy output from the applicators in order to produce the desired heating pattern as indicated by the temperature sensing devices in the applicators.

In one embodiment, the electromagnetic capacitive applicators are connected to an applicator multiplexer which includes an attenuator controlled by the control device. The multiplexer enables one of several groups of applicators to be powered whereby the groups may include different numbers of applicators.

BRIEF DESCRIPTION OF THE DRAWINGS

The novel features believed characteristic of this invention are set forth in the appended claims; however, this invention can be best understood by referencing the Detailed Description of the Embodiment together with these drawings.

DESCRIPTION OF THE PREFERRED EMBODIMENT

This invention relates to a system for the treatment of cancer by hyperthermia. Specifically, the system includes several microwave or UHF capacitive applicators that are inserted into living tissue in a dielectric catheter in or around a cancerous growth. EM energy is then distributed to these applicators which together provide a capacitive EM field in the tissue which is used to heat the cancerous growth to a temperature which destroys the cancerous growth but leaves the normal living tissue surrounding the cancerous growth unharmed. In this invention, the applicators include an enlarged diameter EM energy coupling metal shaft at the tip and a temperature measuring capability enabling the system to provide EM energy and determine the resulting heating of tissue surrounding the applicators.

Figure 1:
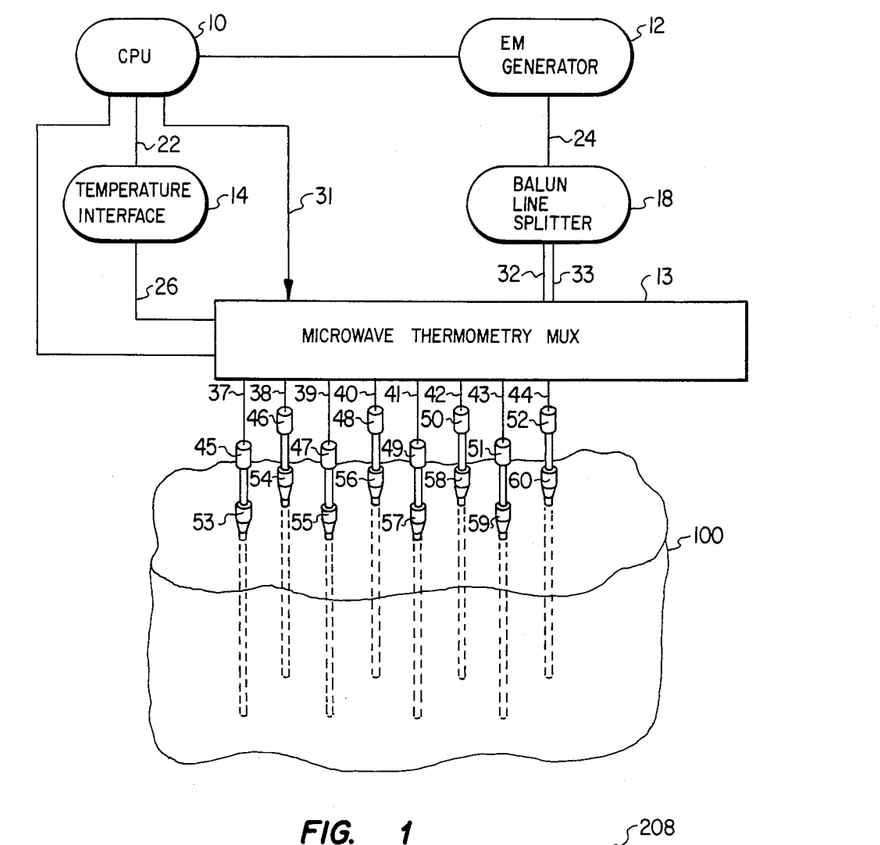
FIG. 1 is a block diagram of the capacitive coupling electromagnetic hyperthermia apparatus.

FIG. 1 is a system block diagram of a typical system of the present invention. The system includes a microwave or UHF generator 12 that is connected by an RF power transmission line 24 to a Balun line splitter. The Balun splitter 18 distributes RF power between two coaxial lines 32 and 33 to the microwave thermometry multiplexer 13.

The multiplexer is connected to typically two to sixteen probes via RF coaxial transmission lines. For instance, the microwave thermometry multiplexer 13 is shown in FIG. 1 connected to eight RF transmission lines 37–44 that are respectively connected to eight applicators 45–52. The applicators are inserted inside eight catheters 53 to 60 which have been placed in the human tissue 100 around the area to be heated.

Figure 2:
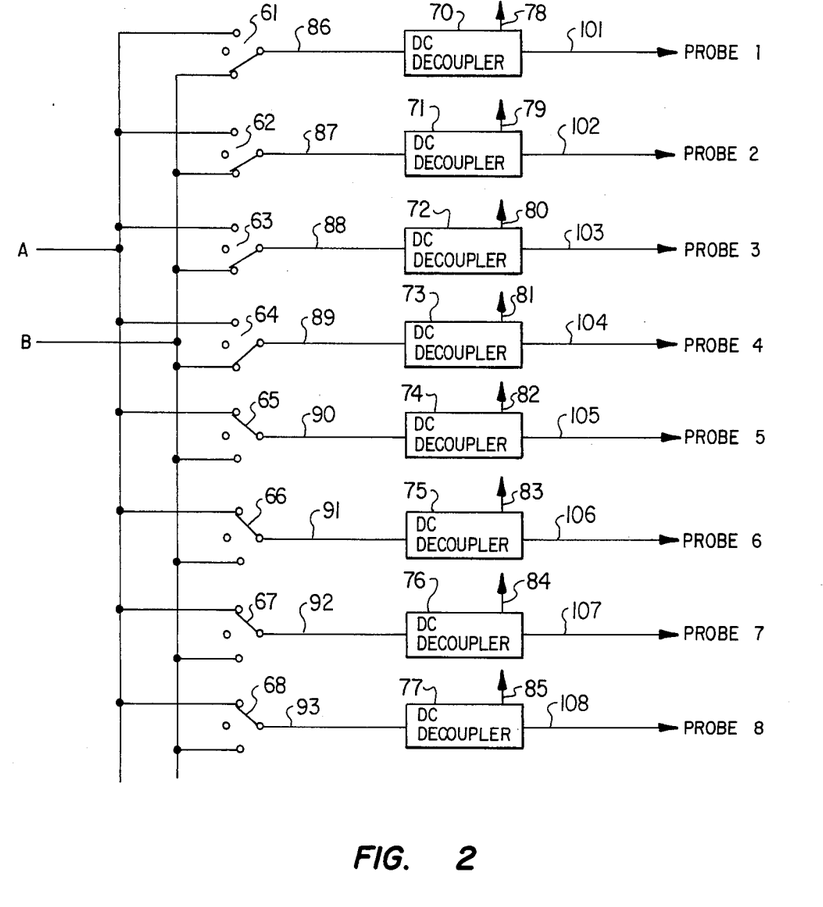
FIG. 2 is a block diagram of the microwave thermometry multiplexer for connecting the applicator electrodes.

The amount of average power provided to each applicator is controlled by its respective multiplexer switch setting. The control of the switch position may be manual or may be controlled by a central processing unit 10. In FIG. 2, the 8 switches 61–68 are each connected to one of the two opposing phase input lines A and B represented by lines 32 and 33. When controlled by the CPU line 31 would actuate switches 61 to 68 as relays by cable 31. In this manner, the central processing unit 10 may control the amount of average RF power distributed to each of the applicators 45 to 52. It should be understood that the switches may also be replaced by any means for regulating power distribution to the applicators such as attenuators, amplifiers, mismatched tuning sections or the like.

The applicators 45–52 may include temperature sensors. The temperature sensors are also connected to the microwave thermometry multiplexers 13 through the respective lead lines as shown. The output of the temperature sensing devices is connected to the temperature interface circuitry 14 via a cable represented by line 26 from the connected multiplexer as shown. The temperature sensor information is then provided to the central processing unit 10 via line 22. In practice, the output of the microwave thermometry multiplexer may be a single multiplexed line for all the sensors connected to the multiplexer or it may be individual discrete lines from each of the applicators to the temperature interface circuitry 14. The central processing unit 10 will be able to adjust the amount of average power to the applicators in accordance with the indicated temperatures to treat the tissue area with a predetermined heating pattern. During treatment, the central processing unit 10 will monitor the indicated tissue temperatures from the applicators and make whatever adjustments are necessary to the capacitively coupled EM power distributed to the applicators.

The implementation of the timing of the RF power and temperature monitoring is important to insure the accuracy of heating of the tissue. However, the applicator can be designed to provide adequate temperature accuracy without the need of special timing of RF power and temperature monitoring.

In one implementation, power is applied to the individual applicators while temperature is measured. Power is then turned off to allow the temperature sensors to cool wherein again temperature is measured. Since the tissue requires more than two seconds to substantially cool, by turning the power off the temperature may be accurately measured since the temperature sensors will normally cool off much faster than the two seconds. By switching RF power on and off from the microwave generator 12, the temperature sensors may be calibrated to determine what portion of the temperature increase during the power on is generated by the heating of the temperature sensors themselves. The central processing unit 10 is then used to regulate the amount of power applied to each of the applicators to produce a specified heating pattern in the body tissue 100. If the temperature sensors do not heat up sufficiently to result in a discrepancy of reading during the application of RF power, the temperature measured during the application of RF power to the body tissue 100 will be used to control the resulting heating pattern. This characteristic can be obtained by proper applicator design described in the applicator details.

A further system enhancement includes the independent control of amplitude and phase to control the heat pattern. This would improve the capability to provide the desired heat patterns. Since lines A and B (32 and 33) are 180 degrees out of phase the switches (61–68) shown for each applicator can be connected to either line A or B or to an open connection.

MULTIPLEXER

Clinical use of this system of FIG. 1 will vary in the number of applicators actually required for use. Typically, between 2 and 16 applicators will be used. To improve clinical use and speed of the changing of the number of applicators. The probes will attach to a coax quick disconnect connector to the multiplexers.

FIG. 2 is a block diagram of multiplexer 13. In practice, multiplexer 13 may contain many more applicator channels than shown. Each probe is connected to an individual decoupling circuit such as 70 to 77 as shown. The DC decoupling circuit includes a simple capacitance and inductance to provide a DC direct current signal on the DC lines 78 to 85 which may be multiplexed or discretely connected to the temperature interface circuitry previously discussed. The DC coupling circuitry 70 further provides the RF connection between the switch 61 via line 86 to the probe via line 101 as shown. In this manner, the probe receives the RF power while providing a direct current temperature sensing indication signal.

In the embodiment shown in FIG. 2, each of the switches 61–68 provide the connection to a group of applicators. All applicator probe outputs need not be connected for fewer operating applicators. At least one applicator must connect to channel A and at least one must connect to channel B to enable current to flow between channel A and B through the tissue to be heated.

APPLICATOR

Figure 3:
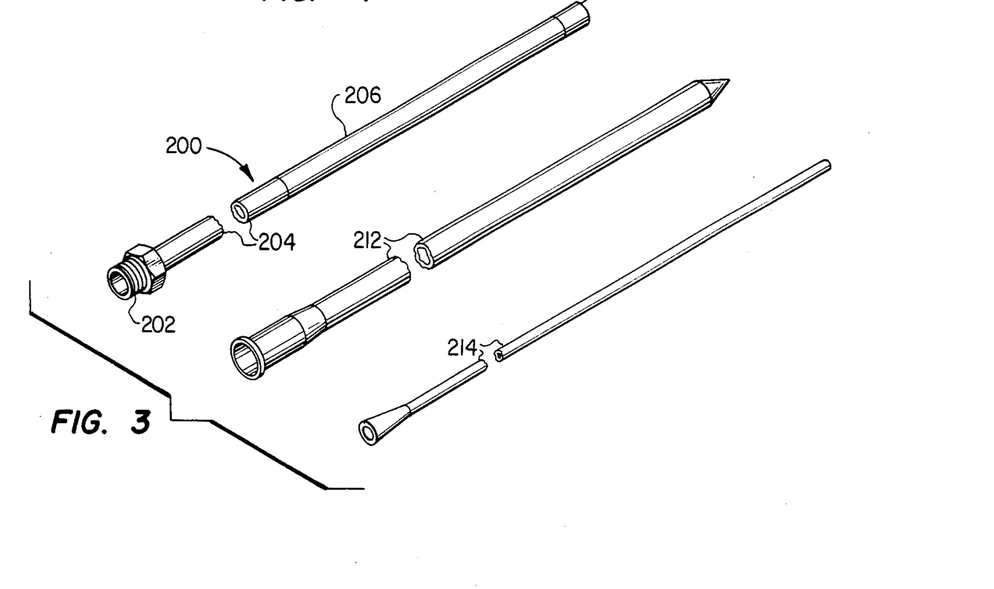
FIG. 3 is a plan view of a capacitive coupling applicator, a catheter, and a hyperdermic needle.

FIG. 3 illustrates the applicator 200 together with a catheter 212 and a hypodermic needle 214. In the preferred embodiment, the catheter 212 is dry catheter (i.e. closed tip) and will be inserted into the body tissue. In practice, the catheter is a 16 gauge catheter. The applicator 200 will then be inserted inside the catheter 212. The applicator 200 includes the connection 202 and a coaxial cable shown as 204, and small wire twisted lead section having an outside coating 206 and terminating with a tip 208. The blunt tip hypodermic needle 214 is provided to indicate the relative size of the applicator and catheter. The blunt tip needle can be used inside the catheter to stiffen the catheter during insertion into the tissue and then removed. The catheter can also be inserted by a larger removable hollow hypodermic needle.

Figure 4:
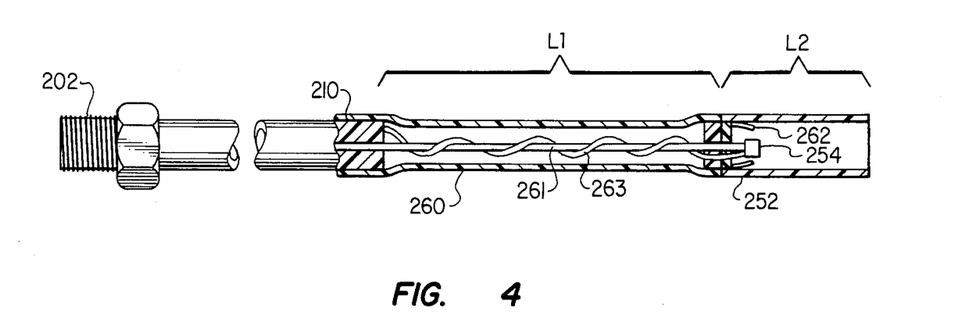
FIG. 4 is a partial sectional view of a capacitive coupling applicator.

The interior of the applicator is illustrated in FIG. 4 as a partial cross-sectional view. The connector 202 is connected to a lead line as shown in FIG. 1. FIG. 4 illustrates that the applicator consists of two lengths L1 and L2, where L1 is the length of the small diameter conductor with an outer dielectric sleeve shown as 260 and L2 is the length of the enlarged diameter tip conductor tube 252 portion including the metallic tip connected to the center conductor 261. The conductor attaches to a threaded or snap on connector 262 connected to the coax center conductor 261 and temperature sensing device 254 typically a thermistor. The coax outer 210 is connected to a conductor 263 which is wrapped around and insulated from the center dielectric 261. Wires 261 and 263 are connected to the temperature sensor 254. These wires are insulated by a dielectric sleeve 260.

Shown in this embodiment is a thermistor 254 that is connected to the outer conductor 210 by a resistive conductor 263. A resistance of over 50 kilo-ohm will prevent a significant RF voltage across the thermistor with typically a 5 megohms resistance at 25° C. In practice, the applicator provides EM capacitive coupling through the dielectric catheter selectively from the enlarged tip 252 while providing a temperature indication of the region from the resulting resistance of thermistor 254. Here the outer conductor 210 is cut back from the tip to expose the small diameter center conductor 261 as shown. The coaxial dielectric insulator may be used to insulate the resistive conductor 263. The 5 megohms thermistor 254 between the center conductor 261 and the lower resistance (typically 100 kilo-ohms) resistive conductor 263 add in series to enable the accurate measurement of temperature. In practice, the thermistor 254 is a microscopic chip that is inserted between the two leads conductor 261 and the resistive conductor 263 as shown. The resistance of the thermistor 254 changes as temperature changes. Therefore, by placing a DC voltage across the outer conductor 210 and center conductor 261, the resulting measured resistance indicates the temperature of the tip region.

The location of the thermistor inside the enlarged tip conductor enables the small mass thermistor to remain basically at the metal tip region temperature. If insufficient resistance is in lead 263 heating for the thermistor may occur because of the presence of the RF field. However, by determining the slopes of cooling, the heat resulting from the selective RF power absorption of the thermistor may be distinguished from the temperature of body tissue.

The approximate capacitance of the interface between the tissue and the enlarged tip metal tube (252) can be determined by the following equation:

$$C = \frac{2\pi E_o E_r}{\log_e(b/a)}, f/m$$

Where $E_o$ is permittivity of space which is $8.85 \times 10^{-12}$ farad/meter, $E_r$ is the dielectric relative permittivity, b is the catheter outer diameter and a is the catheter inner diameter. The tip (252) is assumed to fill the catheter opening. The capacitive coupling impedance is:

$$X_c = -j\frac{1}{\omega c}, \text{ohms}$$

where $\omega c$ is radians per second. For standard 16 gauge teflon catheter $E_r=2$ b=0.066 inches and a =0.043 inches. So the capacitance at the tip is 260 picofarad/meter of length. This is −j205 ohms at 100 MHz for a 3 cm long tip.

The center conductor 261 for this size applicator is typically 0.008 inches in diameter.

Assuming the dielectric sleeving 260 is also teflon and fills the inside of the catheter, the capacitance from lead 261 and the tissue can also be calculated using a modified value for a as 0.008 inches. The value of C for lead 261 is 53 picofarads/meter. For the 100 MHz and 3 cm length example this would be an impedance of −j 1,006 ohms. Some heating is to be allowed in the tissue surrounding lead 261, but the intent of this invention is to provide increased heating at the local tip zone defined by a selectable length (L2) tip zone. The current flow from the applicator into the tissue is divided inversely proportional to the total resistive values loading the local applicator locations. As long as the tip 252 and lead wire 261 lengths are much less than a quarter of a wavelength long, the inductance of the lead will be small. This will place the lead 261 at the same electrical potential as the tip (252).

Figure 5:
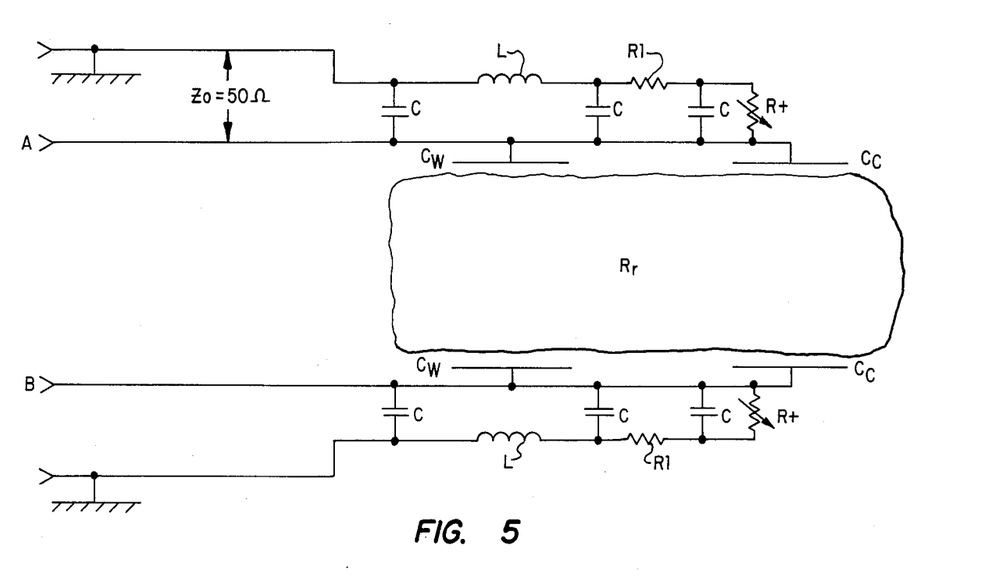
FIG. 5 is a schematic diagram of a pair of capacitively coupled applicators.

FIG. 5 shows an equivalent schematic diagram representing the capacitance of the tip region $C_c$ and the capacitance of the wire region $C_w$. Each are loaded by muscle tissue which has a complex dielectric constant $K^*$ of 160−j72 at 100 MHz. The tissue resistivity is $r = -j/K^* E_o \omega$, ohm-meters or $r=0.42-j0.94$, ohm-meters. For a 3 cm length this is a tissue resistance $R_r$ of approximately $R_r=14-j31$ ohms. Since $R_r$ is so much lower than the impedance of $C_w$ and $C_c$, the amount of current flow along each capacitance $C_w$ and $C_c$ is dominated by the capacitive impedance of $C_w$ and $C_c$. In fact, the current division is inversely proportional to these capacitive impedances.

Therefore, within a 3 cm tip section of enlarged diameter at 100 MHz the impedance is −j205 ohms. The same distance for the conductor 261 provides a −j1,006 ohms. The resulting current density ratio flowing into the tissue from the tip compared to that of the wire 261 is 1,006/205=4.91. Since the power absorption in the tissue is proportional to the current squared, the power density is 24 times higher around the tip 252 for this example than around conductive small diameter connection wire 261. Therefore, selective heating of tissues around the enlarged tip region is the result.

As frequency is increased or wire 261 lengthened, the inductance of the small diameter can begin to increase, the inductance of this lead will add in series with the lead connecting $C_w$ and $C_c$ on the diagram of FIG. 5. This may result in some increase heating around conductor 261 with a corresponding decrease around the tip 252. Therefore, dimensional limits exist on the upper frequency that is permitted for a length L1 of conductor 261. In practice, the maximum length L1 in inches is related frequency in MHz by the following relationship.

L1<1350/f (MHz), inches

Other calculations have concluded that at 100 MHz, the density of power dissipation within a nylon or teflon catheter is less than 0.01% of that of muscle near the electrodes. As the frequency is reduced, the larger capacitive impedance of the catheter walls will increase this power dissipation in the catheter. This catheter heating approximately increases with the inverse square of frequency so at 1 MHz the catheter heating would be approximately the same as the tissue heating. This may result in the nylon melting. To avoid this and excessive muscle and nerve tissue stimulation the frequency recommended should exceed 1 MHz.

In one embodiment where conductor 263 is a low resistance, the actual tissue temperature would be measured when RF power is low or 0 to avoid additional temperature rise of the thermistor while the thermistor is exposed to the RF fields. Since the resistance is measured, the change in resistance resulting from an implied RF power field may be used to measure the power. The DC resistance is the same as the RF resistance for very small chip thermistors. It is important to use a high impedance thermistor to avoid excessive thermistor heating. By using a thermistor small enough to be substantially heated by typically applied RF power, the rapid heating response of the small thermistor to the RF power can be distinguished from the slower tissue temperature rise. Since the applicator is generally used inside a dielectric catheter, the thermal time constant of the sensor to the outer tissue heating is typically two seconds or more. The thermal response time of the thermistor to its own heating from RF energy is much faster however. The timing of a power input pulse with before, during, and after readings can provide a measure of both the RF voltage at the probe radiating tip and the neighboring tissue temperature. The measured RF voltage field would provide a relative measure of the RF power radiated from each of the several applicators in array. Thus, the radiating power balance could be obtained for several applicators as well as the tissue temperatures near each.

A second embodiment of the applicator has the resistance of conductor 263 larger in order to minimize the heating of the thermistor from RF fields along the wires connecting to it. In this preferred embodiment, the thermistor 254 is placed towards the tip spaced from the connection of the conductor 252 and the connector 262 so as to be away from the intense microwave field outside the conductor 252. The tip metal tube 252 is typically between 1 to 10 centimeters long (length L2). The thermistor is substantially within the applicator heating pattern. The thermistor is connected to the center conductor 261 directly. The other side of the thermistor 254 is connected to the outer coax conductor 210 through a thin carbonized lead 263 having high resistance typically 0.01 to 1 megohm. Since the RF radiation resistance is about 50 ohms, and the high resistive lead 263 is in parallel to or twisted around the center conductor 261 (space within a thin dielectric), the shunt capacitance between the resistive lead 263 and the center conductor 261 provide a distributed resistance and capacitance network as shown in FIG. 5.

In FIG. 5, $R_t$ is the thermistor resistance, L represents the distributed lead inductance $R_1$ is the resistive lead resistance, C is the distributed shunt capacitance, $R_r$ is the radiation tissue resistance and $C_c$ is the catheter wall capacitance. This circuit of FIG. 5 shows that when $R_t$ and $R_1$ are high, at high frequencies the capacitive impedance between the inner conductor and the resistive lead will filter the amount of RF current reaching $R_t$. Since the whole circuit is loaded with the tissue resistance $R_r$ through the catheter wall capacitance $C_c$, the only DC resistance measured is $R_t$ in series with $R_1$. So $R_1$ should be much less than $R_t$ so as not to substantially modify the temperature dependence of $R_t$. However, $R_1$ should be high enough to provide some RF current filtering to reduce thermistor heating. In the preferred embodiment, the 5 megohms thermistor (at 25° C.) have been tested and its value at 52° C. is 2 megohms.

The advantage of this structure is that the thermistor will measure the temperature of the surrounding area without regarding to the RF power level. In other words, the thermistor RF heating is minimal. This means that the temperatur sensors may be easily calibrated. Testing of the prototypes of this design resulted in the amount of local thermistor and applicator heating observed to be much less than 1° at typical clinical power levels at 5 watts. Here the electric field is very concentrated as well as the current flowing into the center conductor. The thermistor temperature is primarily a result of three parts: thermistor heating, coaxial center conductor heating, and surrounding tissue heating. The mass of the surrounding tissue is much larger than the mass of the thermistor, metal cover and outer conductor. When RF power is turned off, the thermistor and conductors will cool much faster than the tissue. The interconductor heating therefore is the highest. From testing it was determined that the outer conductor heating is 16% of the heating of the interconductor. The thermistor heating is only about 5% of the conductor heating. The measured response of thermistor cooling from selective thermistor heating for the prototype applicators were observed to be typically below 250 milliseconds after the RF power had been turned off. The temperature can be calculated by measuring the resistive change of the thermistor with a DC decoupling circuit remotely located on the RF power input circuit (the multiplexer as previously discussed). This temperature change may be used to measure the relative radiating power from each applicator. The resistive equation for the thermistor is:

$$R = \frac{A\,e^{(D/T)}}{T^c}$$

where R is the resistance, T is the temperature in Kelvin degrees, and A, D, and C are constants found by a three temperature calibration technique. The general form of this equation can be approximated by:

$$A\,T^2 + TB + C = T^2 \ln(R)$$

when R is measured at three different temperatures, the constants of calibration may be found by solving the three equations simultaneously.

The change in temperature is directly proportional to the power input. So the power balance can be determined by comparing the relative temperature changes, observed as the RF power is turned off for about one second. In an array, these temperature change measurements could guide an operator in monitoring adjustments of the power balance of several applicators. Having measured the various temperature changes of cool down after RF powers turned off, these values can be substracted from the measured temperatures while the power is on. If the total input power is changed to all applicators, the resulting change in temperature expected on all the applicator temperature sensors could be estimated as being proportional to the power change until the next RF power off sequence (typically every 30 seconds). When conductor 263 is a high resistance little change of thermistor temperature will initially occur between RF being on or off.

A further embodiment of this invention includes an applicator having a fiber optics temperature sensor contained in the dielectric. The temperature sensor would be connected to the multiplexer by fiber optic lines. A fiber optic structure for measuring temperature is illustrated in U. S. Pat. No. 4,136,566 which is herein incorporated by reference. Other means of optically determining are disclosed in the paper entitled "Thermometry Considerations in Localized Hyperthermia" by T. C. Cetas and W. G. Conner printed in Medical Physics, March/April, 1978. By placing a fiber optics temperature sensor and fiber optic connecting lines in the dielectric of the radiating applicator, the temperature along several different regions may be measured without providing any electrical disturbance to the radiating portion of the applicator.

Figure 6:
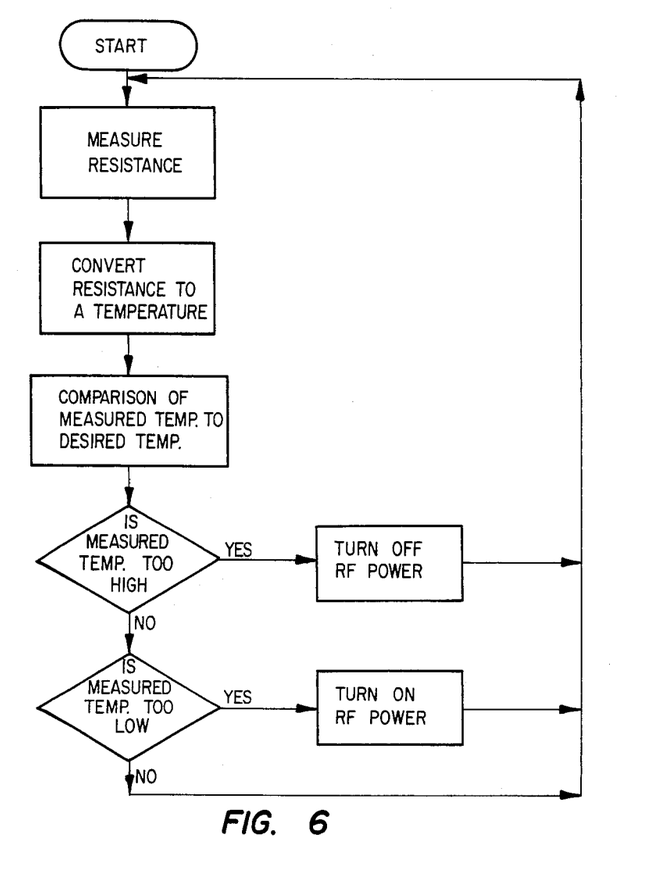
FIG. 6 is a software flow chart of the software used to calibrate the temperature sensing thermistor of the capacitive coupled applicator, and correct for any local thermistor heating resulting from RF potentials across the thermistor.

FIG. 6 illustrates a software flowchart of the software that would be normally executed by the central processor unit 10 of FIG. 1. The CPU uses the temperature measured at the applicator locations to adjust power transmitted to conform to a preselected heating pattern. Using applicators with several temperature sensors, a three dimension heating pattern may be detected which, with attenuator and phase relationship adjustments, may be used to more exactly provide treatment.

Although preferred embodiments have been described in detail, it should be understood that various substitutions, alternations and changes may become apparent to those skilled in the art. These modifications may be made without departing from the scope and spirit of the invention as defined by the appended claims.

What is claimed is:

1. An electromagnetic hyperthermia system for heating local regions of body tissue, said system comprising:
a source of electromagnetic energy;
a power divider connected to the source for distributing the electromagnetic energy, a plurality of power control means including at least an A channel and a B channel connected to the power divider for receiving the electromagnetic energy and controlling the electromagnetic energy conduction, a corresponding number of plurality of capacitive type applicators connected to the plurality of power control means, a plurality of tube means for insertion into the body tissue in or around a cancerous growth, each of said plurality of tube means adapted to receive an applicator of the corresponding number of plurality of capacitive type applicators, said plurality of capacitive type applicators being mounted in the plurality of tube means for acting as electrodes of which at least one electrode is connected to channel A and at least one electrode is connected to channel B for enabling current to flow between channel A and channel B through the tissue to be heated and said plurality of capacitive type applicators further including temperature sensing means for providing an indication of adjacent body tissue temperatures; and a data processing means connected to the source, the plurality of power control means and the temperature sensing means for controlling the amount of heating in accordance with a desired heating pattern.

2. An electromagnetic hyperthermia system according to claim 1 wherein said plurality of power control means regulates the amplitude and phase of electromagnetic radiation transmitted to each applicator.

3. An electromagnetic hyperthermia system according to claim 1 wherein said power control means provides power to pairs of applicators in order to provide the capacitive coupling of electromagnetic radiation.

4. An electromagnetic hyperthermia system according to claim 1 wherein each tube means of the plurality of tube means is a dielectric tube.

5. An electromagnetic hyperthermia system according to claim 4 wherein each dielectric tube is a catheter.

6. An electromagnetic hyperthermia system according to claim 1 wherein each applicator of the plurality of applicators includes first and second lengths having dielectric sleeves of first and second diameters, and first and second metal sections mounted respectively within said first and second dielectric sleeves, said first and second metal sections including, respectively, a centrally disposed conductor and an elongated tip, the centrally disposed conductor having a diameter substantially smaller than the diameter of the elongated tip, whereby the capacitance at the elongated tip through the dielectric sleeve into the surrounding tissue is substantially greater than the capacitance at the centrally disposed conductor through the dielectric sleeve into the surrounding tissue for more selective heating of the surrounding tissue.

* * * * *